United States Patent [19]

Berti et al.

[11] 4,247,297

[45] Jan. 27, 1981

[54] TEST MEANS AND METHOD FOR INTERFERENCE RESISTANT DETERMINATION OF OXIDIZING SUBSTANCES

[75] Inventors: Giovanni Berti, Coma, Italy; William I. White, Elkhart; Rodric H. White-Stevens, Howe, both of Ind.

[73] Assignee: Miles Laboratories, Inc., Elkhart, Ind.

[21] Appl. No.: 14,693

[22] Filed: Feb. 23, 1979

[51] Int. Cl.³ .................... G01N 31/22; G01N 33/52; C12Q 1/28; C12Q 1/62

[52] U.S. Cl. .................... 23/230 B; 23/901; 23/904; 23/913; 23/925; 23/932; 252/408; 422/56; 435/4; 435/10; 435/14; 435/28; 435/805

[58] Field of Search .................... 23/230 B, 913, 901; 422/56; 252/408; 435/28, 4, 10, 14, 805

[56] References Cited

U.S. PATENT DOCUMENTS

| | | | |
|---|---|---|---|
| 3,627,698 | 12/1971 | Rey | 422/56 |
| 4,089,747 | 5/1978 | Bruschi | 435/10 |
| 4,101,381 | 7/1978 | Klose | 435/14 |
| 4,119,405 | 10/1978 | Lam | 435/28 |

*Primary Examiner*—Sidney Marantz
*Attorney, Agent, or Firm*—Charles J. Herron

[57] ABSTRACT

Test means, such as a composition or device, method of making a test device and process for determination of at least one oxidizing substance, such as a peroxide, are disclosed. More particularly, the contemplated test means comprises a hydrazone and 8-amino-1-napthol-5,7-disulfonic acid (Chicago acid). Further provided is a test system for the determination of a constituent in a sample, having means responsive to the presence of said constituent in said sample to produce at least one oxidizing substance and a composition for determining said at least one oxidizing substance, wherein said composition comprises a hydrazone and 8-amino-1-napthol-5,7-disulfonic acid (Chicago acid). The test system is preferably of the type which determines peroxides formed from enzymatic conversion of constituents in biological fluids. When in the form of compositions the test means can optionally be incorporated with a carrier, such as a tablet or matrix, to provide a test device. The test system is highly sensitive to low levels of body fluid constituents to be detected, while also being highly resistant to interfering reducing substances, such as ascorbic acid, often present in body fluids.

20 Claims, 2 Drawing Figures

TEST MEANS AND METHOD FOR INTERFERENCE RESISTANT DETERMINATION OF OXIDIZING SUBSTANCES

FIELD OF THE INVENTION

The present invention relates generally to the field of diagnostic tests and, more particularly, to those tests useful in qualitative and quantitative determination of biological components, such as glucose and uric acid, in which tests such components are converted to an oxidizing substance, such as a peroxide.

BACKGROUND OF THE INVENTION

Glucose oxidase enzymatically converts glucose to gluconic acid and hydrogen peroxide. The hydrogen peroxide thus formed can be reduced to $H_2O$ by a peroxidatively active substance in the presence of an indicator system which is oxidized to produce a response, such as a color change. The chromogenic indicator o-tolidine has been used for some time in glucose test systems, but provides results which are subject to reduction of the oxidized indicator by interfering substances, such as ascorbic acid. Further, the safety of o-tolidine has been questioned.

Likewise, uricase enzymatically converts uric acid to allantoin and hydrogen peroxide. The hydrogen peroxide formed can be reduced to $H_2O$ by a peroxidatively active substance in the presence of an indicator system, historically o-dianisidine.

More recently, Gochman and Schmitz have reported using 3-methyl-2-benzothiazolinone hydrazone hydrochloride with N,N-dimethylaniline to form an azo dye indicator in determinations of uric acid, *Clin. Chem.* 17:1154 (1971), and glucose, *Clin. Chem.* 18:943 (1972). Even though it is asserted that the mixture with N,N-dimethylaniline was more resistant than o-tolidine, susceptibility to ascorbic acid interference produced significant error in reported uric acid and glucose concentrations.

The mechanism of oxidatively coupling heterocyclic hydrazones with phenols, aromatic amines and other compounds in the classic azo coupling reaction is reviewed briefly in Zollinger, Azo and Diazo Chemistry, Interscience, New York, p. 215–217 (1961). A summary of the original work, directed to the formation of azo dyes by oxidative coupling, of Hünig and co-workers in Germany (1957–68) is incorporated in Baer, *Cationic Dyes for Synthetic Fibers,* Venkataraman (ed.), The Chemistry of Synthetic Dyes, Vol. 4, Academic Press, N.Y., pgs. 188–193 (1971).

Hunziker, U.S. Pat. No. 3,979,262, adds a buffer, of citric or maleic acid, to the mixture of Gochman et al., supra, and discloses that, along with N,N-dimethylaniline, other aromatic amines can be used so long as they are not substituted in both the ortho and para positions. The buffer is also critical and maintains a predetermined pH range of from 3.2 to 4.7 for a uric acid determination and from 4.7 to 5.5 for a glucose or cholesterol determination.

The prior art, insofar as it teaches the use of hydrazone indicators in analysis for $H_2O_2$, suggests that the reaction between 3-methyl-2-benzothiazolinone hydrazone (MBTH) and dimethylaniline is resistant to the effects of reducing substances in a sample. While this may be true relative to indicators such as o-tolidine, the use of such hydrazone indicators provides very poor indications in the presence of ascorbate.

Therefore, efforts by these prior workers have failed to provide an indicator system which is either substantially free of susceptibility to the effects of interfering substances or makes use of indicators recognized for their safety.

Recently issued U.S. Pat. No. 4,119,405 discloses the use of 4,5-dihydroxy-2,7-napthalene disulfonic acid and 1-hydroxy-2-naphthalene sulfonic acid as hydrazone couplers. Unlike the couplers of Hunziker, these compounds are not amines. While much superior to the couplers theretofore available, their freedom from ascorbate sensitivity still leaves room for improvement.

OBJECTS OF THE INVENTION

It is therefore an object of the present invention to provide an improved test for the detection of oxidizing substances in body fluids.

It is another object of the invention to provide an improved test for those oxidizing substances which are enzymatically converted from other clinically significant body fluid components.

A further object of the invention is to provide an improved test for the detection of oxidizing substances in body fluids which is highly resistant to interfering reducing substances.

A still further object of the invention is to provide an improved test for the detection of oxidizing substances wherein the above-identified advantages are achieved through a novel indicator system comprising a hydrazone and 8-amino-1-napthol-5,7-disulfonic acid (Chicago acid).

Other objects and a fuller understanding of the invention will be had by referring to the following description and claims drawn to preferred embodiments thereof, taken in conjunction with the accompanying drawings in which:

SUMMARY OF THE INVENTION

Figure 1:
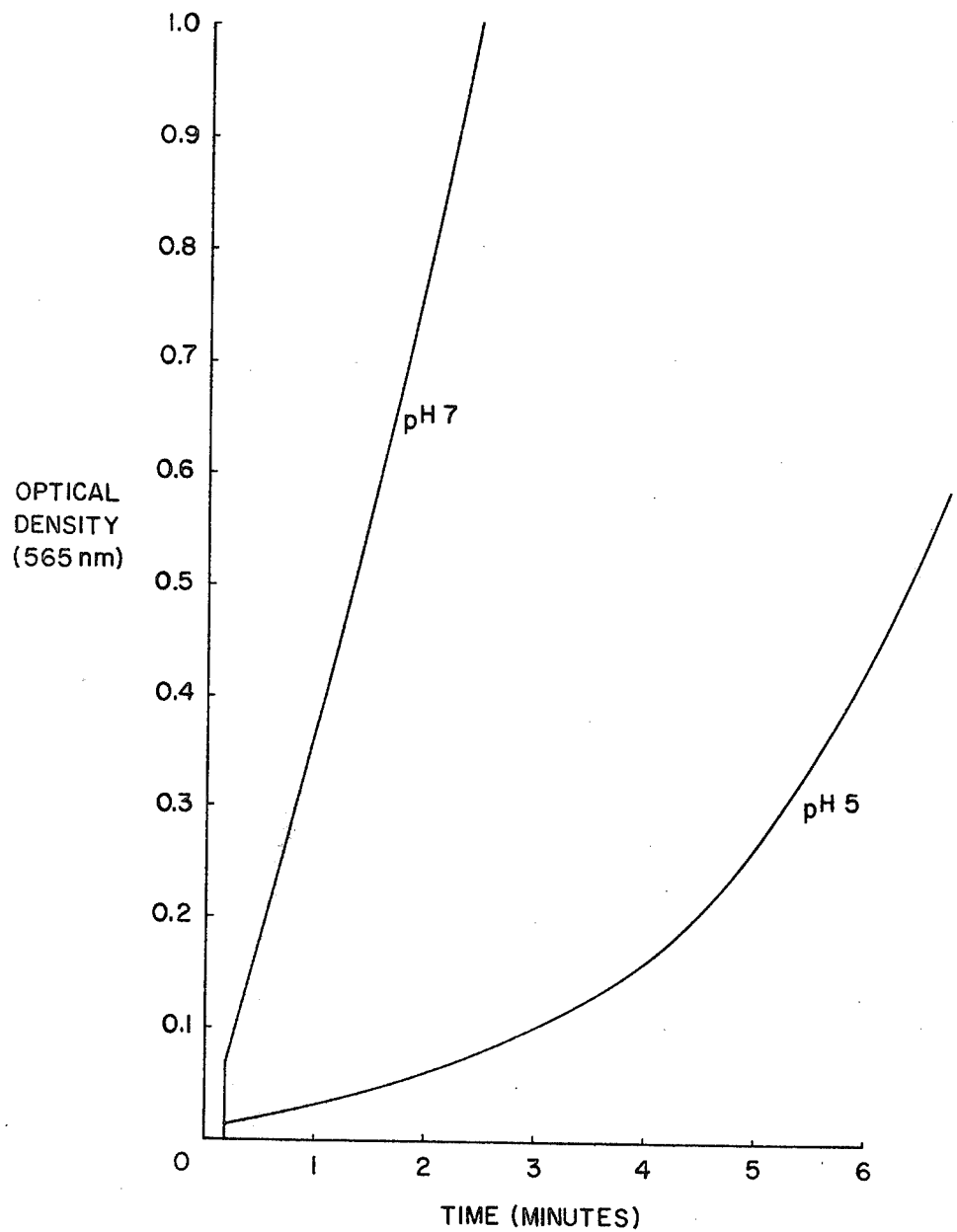
FIG. 1 is a graphical representation of the data reported in Example III for MBTH/Chicago acid in accordance with the invention tested in the presence of ascorbic acid at different pH levels, obtained by plotting optical density (OD) vs. time.

In accordance with the present invention there are provided test means, such as a composition and device, a method of making the test device, and a process for determination of at least one oxidizing substance, such as a peroxide. More particularly, the contemplated test means comprises a hydrazone and 8-amino-1-napthol-5,7-disulfonic acid (Chicago acid). Further provided is a test system for the determination of a constituent in a sample, having means responsive to the presence of said constituent in said sample to produce at least one oxidizing substance and a composition for determining said at least one oxidizing substance, wherein said composition comprises a hydrazone and 8-amino-1-napthol-5,7-disulfonic acid (Chicago acid). The test system is preferably of the type which determines peroxides formed from enzymatic conversion of constituents in biological fluids. When in the form of a composition the test means can optionally be incorporated with a carrier, such as a tablet or matrix, to provide a test device. The test system is highly sensitive to low levels of body fluid constituents to be detected, while also being highly resistant to interfering reducing substances, such as ascorbic acid, often present in body fluids.

In the test system, the means responsive to the presence of the constituent in the sample to produce at least one oxidizing substance can include glucose oxidase for glucose determination, or uricase for uric acid determination and a peroxidatively active substance. Typical of such peroxidatively active substances are peroxidase or hemoglobin, used when hydrogen peroxide is the oxidizing substance.

In contrast to proir art compositions, that of the present invention is highly sensitive to low levels of body fluid constituents to be detected, while also being highly resistant to the effects of competitive reducing substances, particularly ascorbic acid in urine. Since a characteristic color reaction takes place depending on the concentration of the oxidizing substance detected, quantitative detection for such body fluid components as glucose and uric acid is possible.

DESCRIPTION OF THE PREFERRED EMBODIMENTS

Although specific terms are used in the following description for the sake of clarity, these terms are intended ro refer only to the particular embodiment of the invention selected for exemplary illustration, and are not intended to define or limit the scope of the invention.

The test means according to the invention can take many physical forms and include many specific hydrazones for coupling with the Chicago acid regardless of the form assumed. Additional materials, such as stabilizing agents, can be employed. The test means can be used in both liquid and solid forms, as can the test system, incorporating a composition of the test means as exemplified by the procedures and embodiments described below.

The hydrazones useful in the test means are condensation products of a hydrazine with an aldehyde or ketone and contain the grouping $>C=NNH_2$. Many hydrazones are capable of oxidatively coupling with hydroxynapthalenesulfonates to form a colored entity. Such include, among others, 3-methyl-2-benzothiazolinone hydrazone, 1-methyl-2-quinolinone hydrazone, N-methyl-pyridone-4-hydrazone, N-methyl-pyridone-2-hydrazone, 1-methyl-quinolinone-4-hydrazone, N-methyl-thiazolinone-2-hydrazone, N-methyl-oxazolinone-2-hydrazone, N-methyl-benzoxazolinone-2-hydrazone and 1,3-dimethylbenzimidazolinone-2-hydrazone. In a preferred embodiment of the composition, a 3-($C_1$-$C_4$ alkyl)-2-benzothiazolinone hydrazone chromogen, such as 3-methyl-2-benzothiazolinone hydrazone (MBTH), is used. Such hydrazones are strong reducing agents.

As used herein the expression "hydrazone" includes the acid addition salts thereof. Any conventional acid addition salt can be utilized such as those formed from hydrochloric acid, hydrobromic acid, sulfuric acid, nitric acid and the like. These acid addition salts can be used alone or they can be used in conjunction with the corresponding hydrazone.

Molar ratios of hydrazone/coupler range from about 17:1 to about 1:17, with more nearly equimolar ratios being preferred for the optimum combination of detection sensitivity and interference resistance.

The composition can further include stabilizing agents, carboxymethylcellulose and polyoxyethylene ethers of fatty alcohols (BRIJ ® made by ICI United States Inc., Wilmington, Dela. 19897) being advantageously selected.

Test means according to the invention, and test systems employing compositions of said test means, are preferably used in a generally neutral or slightly alkaline pH range, although they remain operative even at somewhat lower pH. The maintenance of a generally neutral or alkaline pH provides improved reactivity in terms of speed and resistance to interference, in contrast to the teaching of the prior art.

The test system comprises, along with the composition according to the invention, means responsive to the presence of a constituent to be determined in a sample to produce an oxidizing substance for determination by the composition. Such means are preferably enzymatic in nature. For example, when glucose is to be determined, glucose oxidase and peroxidase are the constituent responsive means. Likewise, when uric acid is to be determined, uricase and peroxidase comprise the constituent-responsive means. The concentrations and types of reagents useful in the constituent-responsive means are contemplated to include those known to the art.

The test means can be used as a solution for determination of oxidative substances in a sample. Further, the test system for determination of constituents converted to such oxidative substances, containing the test means in composition form, can be used in liquid form. The test system is preferably used to detect biological, such as body fluid, constituents by adding the test means to a specimen such as urine, serum, cerebrospinal fluid, tissue culture supernatant or the like. For assays using the test system in liquid form, the peroxidase and/or the oxidase should be segregated from the other reagents until ready for use. The determination is allowed to go forward by introduction of the segregated reagent, such as the peroxidase.

When used in solution, whether in the test means itself or as a composition thereof in a test system, the 8-amino-1-napthol-5,7-disulfonic acid (Chicago acid) is preferablyused in concentrations of from about $10^{-5}$ Molar (M) to about $10^{-3}$ M. Likewise, the hydrazone is preferably used in concentrations of from about $10^{-5}$ M to about $10^{-3}$ M. When one or more stabilizing agents are included, they are preferably present in total concentrations of from about 0.5 milligram/deciliter (mg/dl) to about 5.0 g/dl. When peroxidase is at least one of the reagents comprising the constituent-responsive means of the test system, concentrations of the peroxidase are preferably from about 10 micrograms/liter ($\mu$g/l) to about 500 $\mu$g/l. The solvent used in preparing the solutions can be water, physiological solutions, organic solvents, such as methanol, or mixtures thereof.

Also provided are test devices incorporating the test means or the test system of the invention and a method of making such reagent test devices, which method comprises incorporating a carrier, such as a matrix or tablet, with the test means or test system, respectively. When this incorporation is by impregnation with a solution of the composition according to the invention, including a test system, the carrier so impregnated is then dried. In addition to impregnation, the devices of the present invention can be made by other suitable techniques such as printing or spraying the composition onto a substrate or matrix.

The test device is preferably prepared by a multi-dip process. The concentrations of reagents used in the impregnating solutions range from about $10^{-3}$ M up to a saturated solution. Most generally useful for the hydrazone and coupler is a concentration of about 0.02 M each. Peroxidase concentration is from about 0.015 mg/ml to about 2 mg/ml of solution Solid preparations are preferably incorporated with a carrier matrix in strip format. The term carrier matrix can be envisioned to refer to bibulous and nonbibulous matrices which are insoluble in and maintain their structural integrity when exposed to water or physiological fluids. Suitable bibulous matrices which can be used include paper, cellulose, wood, synthetic resin fleeces, glass fiber, woven and nonwoven fabrics and the like. Nonbibulous matrices include organo-plastic materials such as polypropylene or the like. When a bibulous matrix is employed, the matrix is advantageously affixed by suitable means, such as double-faced adhesive tape, to an insoluble support member, such as an organo-plastic strip, e.g. polystyrene, for ease of use.

Alternatively, the compositions of the invention can be embodied in a carrier taking the form of a pressed or molded tablet containing conventional carrier material The test device is advantageously used by momentarily dipping it in a test sample or by otherwise contacting the carrier matrix with a test sample, whereupon a detectable color change results if oxidative components are present in the sample. The test device can be used in the same way when samples of plasma, serum or other body fluids are tested.

The relationship between K (the absorption coefficient of the specimen), reported in some of the examples, and the concentration of absorbing species (such as uric acid or glucose) is given by the Kubelka-Monk equation which is provided, along with a discussion of reflectance spectrophotometry in Kortümi, G., *Reflectance Spectroscopy*, Springer-Verlag Inc., New York, 1969. K is defined as twice the absorbance/unit path length (2A/b) in transmission measurements. For purposes of this application K is assumed to be proportional to the concentration of colored indicator molecules formed. In the relationship defined by the Kubelka-Monk equation the present reflectance (%R) value decreases as the concentration of oxidative substance detected increases, and vice versa. Thus, the readings taken inversely correlate, according to the equation, with the concentration of absorbing species detected. In the examples herein the readings were taken at the wavelengths ($\lambda$) indicated.

Reflectance readings can be obtained from commercially available spectrophotometers such as Beckman DK-2 Spectrophotometer, Beckman Instruments, Inc., Fullerton, Calif. 92634 or Spectrocolorimeter SCF-1, Israel Electro-Optical Industry Ltd. (distributed in the U.S. by Broomer Research Corporation, Plainwell, Long Island, N.Y. 11803).

Horseradish peroxidase and glucose oxidase were obtained from Miles Research Products, Miles Laboratories, Elkhart Indiana 46515. A copolymer of methyl vinyl ether and maleic anhydride (Gantrez AN-139) and polyvinyl pyrrolidine (PVP) were obtained from GAF Corp., Chemical Products, N.Y., N.Y. 10020). The 3-methyl-2-benzothiazolinone hydrazone hydrochloride monohydrate, other hydrazones, 1-hydroxy-3-napthalene sulfonic acid, 1-hydroxy-5-napthalene sulfonic acid, 3-dimethylaminobenzoic acid, and violet acid (1-naphtol-3,6-disulfonic acid) were obtained from Aldrich Chemical Co., Inc., Milwaukee, Wisc. 53233. Chicago acid was obtained from Pfaltz & Bauer, Inc., Stamford, Conn. 06902. Standard reagent grade solvents and reagents were used.

The examples shown are merely illustrative and are not to be construed as a limitation of the invention. One skilled in the art will be able to make such variations, substitutions and changes in the ingredients and parameters as may seem desirable.

EXAMPLE I

In the experiments described in this example, the relative ascorbate resistance of various MBTH-coupler systems and of o-tolidine are demonstrated.

A first impregnating solution was prepared to contain the following

| | |
|---|---|
| Distilled Water | 40 ml. |
| Ethanol | 40 ml. |
| Gantrez AN 139 5% weight/volume (w/v) in distilled water | 5? ml |
| Tris malonate buffer [2.8 M Tris (hydroxymethyl) aminomethane; 1.4 M malonic acid; 1.4 M Sodium malonate] | 32 ml. |
| Polyvinyl pyrrolidone 10% w/v in distilled water | 28 ml. |
| 200 mg Peroxidase in 4.3 ml glucose oxidase (1000 U/ml) + 19.3 ml distilled water | |

Sheets of Eaton-Dikeman 204 filter paper (E&D) were impregnated to saturation with the above-prepared solution and dried at 80° C.

A first portion of these dried papers was saturated with 0.02 M o-tolidine in $CHCl_3$ and dried at 50° C. to form the o-tolidine devices used. The remaining or second portion of the above-prepared dried papers was then impregnated to saturation with a solution of 50 ml of methanol having 250 mg MBTH hydrochloride monohydrate dissolved therein, and dried at 60° C.

In a third impregnation, paper sheets of the second portion above were respectively impregnated to saturation with the indicated solution of one of the following potential couplers:

| | |
|---|---|
| Chicago Acid | 200 mg in 40 ml methanol |
| Violet Acid | 350 mg in 40 ml methanol + 10 ml water |
| Diethylaniline | 186 mg in 50 ml methanol |

The papers so impregnated were then dried at 60° C. to form devices.

These devices were respectively tested with ascorbate-free 100 mg/dl aqueous glucose solutions and with 100 mg/dl aqueous glucose solutions containing 50 mg/dl ascorbate, and any color changes were read by the use of a recording reflectance spectrophotometer. Reflectance values at specific wavelengths were converted, by the Kubelka-Monk equation described previously, to equivalent absorbance values (K).

A ratio of K values was used in which K for data taken at 1 minute in the presence of 50 mg/dl ascorbate was divided by K for data taken at 1 minute in the absence of ascorbate. A value of 1 would mean no ascorbate interference; a value of 0 would mean complete ascorbate interference. Results are shown in Table 1.

TABLE 1

| | Relative Ascorbate Interference | |
|---|---|---|
| Indicator | λ Observed (nanometers) | K(Glucose + 50 mg/dl Ascorbate) / K (No Ascorbate) |
| o-Tolidine | 620 | 0.01 |
| MBTH- Chicago Acid | 560 | 0.40 |
| MBTH- Violet Acid | 540 | 0.08 |
| MBTH- Diethylaniline (DEA) | 600 | 0.12 |

These data clearly demonstrate that MBTH/Chicago acid had an ascorbate resistance much superior to o-tolidine, and indeed is significantly more ascorbate resistant than the prior art formulas based on MBTH/diethylaniline.

EXAMPLE II

In the experiments reported by this example, MBTH/Chicago acid test devices were prepared as in Example I and respectively tested with samples of ascorbate-free urine and or urine containing 50 mg/dl ascorbate, both urine samples containing 100 mg/dl glucose. The reflectance values observed in the devices tested were converted to equivalent absorbance (K) values, and a ratio of K values was taken as in Example I. The ratio of activity in the presence of ascorbate compared to activity in ascorbate-free testing was 0.89.

When these results are compared with those reported in Table 1 of Example I it is seen that the MBTH/Chicago acid devices were twice as ascorbate resistant when used for testing urine.

EXAMPLE III

Solutions prepared as set forth below with compositions according to the invention were compared with those of the prior art for the effect of pH and buffer variance in solutions with and without ascorbate.

These tests, like those previously reported, compare the reactions of a hydrazone with various couplers in response to an oxidant. In the previous examples the compositions included an oxidase which reacted with the analyte or substance to be detected, to produce an oxidant, $H_2O_2$. Peroxidase was included in those compositions along with the other components and the reaction proceeded upon contacting a sample containing the analyte. In contrast, the test compositions in this example were prepared to contain $H_2O_2$, rather than the analyte-responsive oxidase, and the peroxidase was withheld until time for proceeding with the test.

Test solutions at pH 5.0 were prepared in 0.311 M citrate buffer. Test solutions at pH 7.0 were prepared in 0.093 M Tris [Tris(hydroxymethyl)aminomethane] combined with 0.093 M malonate. In each buffer system, test solutions were prepared to concentrations of 100 μM MBTH, 100 μM coupler, and 333 μM $H_2O_2$. The test solution prepared for each of the couplers was divided into two portions. To one portion of each test solution was added 56.8 μM (1 mg/dl) ascorbic acid.

The above solutions were placed in 3 ml standard glass or quartz cuvettes. In each case the reaction was allowed to proceed by injection of peroxidase to a concentration of 125 nanograms (ng)/ml. As in the previous examples, formation of the chromogenic coupled hydrazone/coupler resulted in a change of optical density. Changes in optical density (ΔOD) were recorded by a standard recording absorbance spectrophotometer with the results shown in Tables 2 and 3.

TABLE 2

| Tris-malonate Buffer (pH 7) | | | |
|---|---|---|---|
| | | Rate of Reaction (ΔOD/min.) | |
| MBTH Coupler | Wave Length | No Ascorbate | Ascorbate |
| Chicago Acid | 565 nm | 0.867 | 0.360 |
| Chromotropic acid | 572 nm | 0.600 | 0.223 |
| N,N-dimethylaniline | — | No reaction | No reaction |
| 1-hydroxy-2-naphthalenesulfonic acid | 495 nm | 0.373 | 0.159 |
| 1-hydroxy-3-naphthalenesulfonic acid | 490 nm | 0.545 | 0.0977 |
| 1-hydroxy-5-naphthalenesulfonic acid | 495 nm | 0.493 | 0.0815 |

TABLE 3

| Citric Acid Buffer (pH 5) | | | |
|---|---|---|---|
| | | Rate of Reaction (ΔOD/min.) | |
| MBTH Coupler | Wave Length | No Ascorbate | Ascorbate |
| Chicago Acid | 565 nm | 0.196 | 0.0282 |
| Chromotropic acid | 572 nm | 0.162 | 0.0065 |
| N,N-dimethylaniline | 570 nm | 0.189 | 0.0000 |
| 1-hydroxy-2-naphthalenesulfonic acid | 495 nm | 0.0891 | 0.0037 |
| 1-hydroxy-3-naphthalenesulfonic acid | 490 nm | 0.0992 | 0.0000 |
| 1-hydroxy-5-napthalenesulfonic acid | 495 nm | 0.0822 | 0.0000 |

Figure 2:
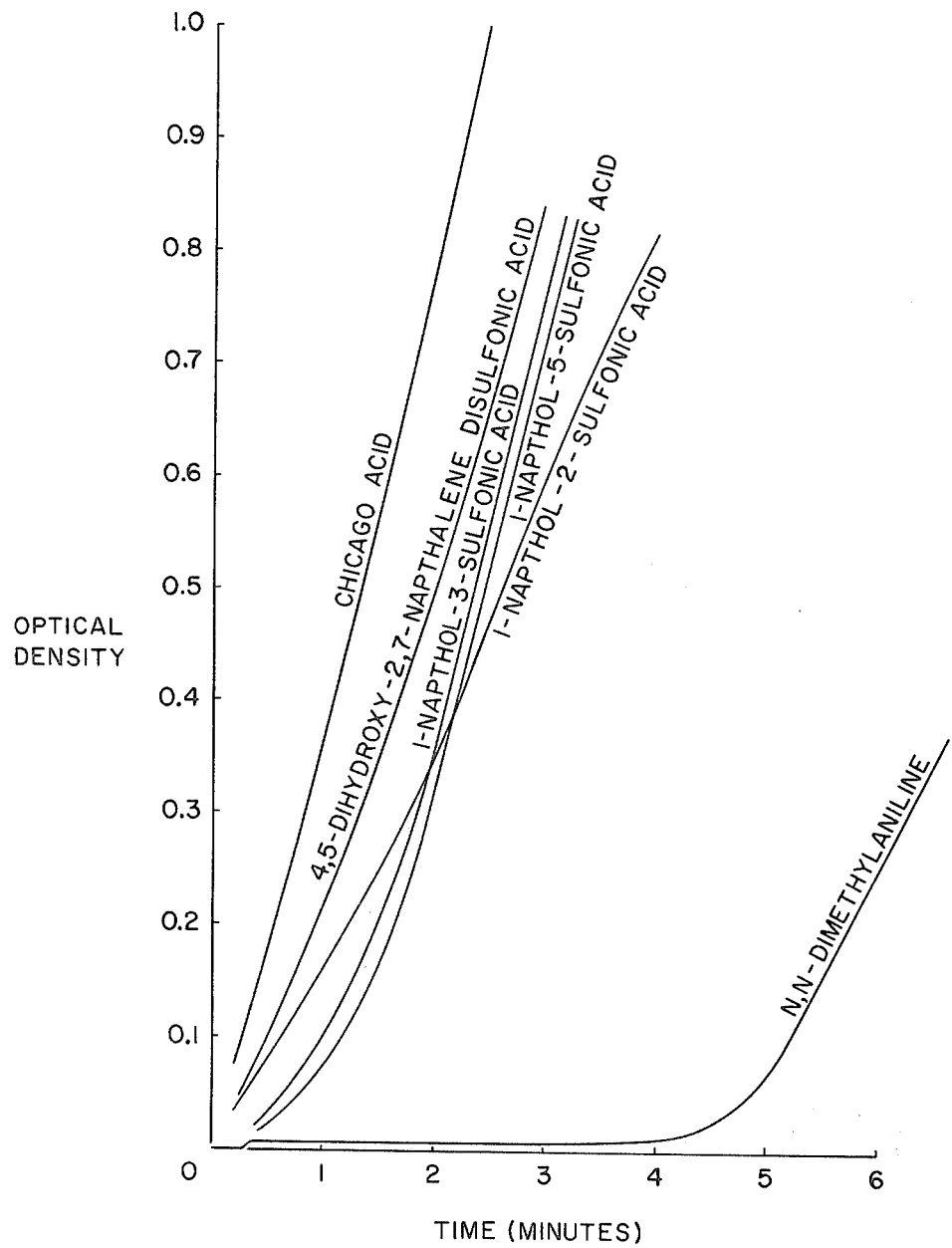
FIG. 2 is a graphical representation of the data reported in Example III for the various MBTH couplers tested in the presence of ascorbic acid in Tris-Malonate buffer (pH 7) with the exception that the dimethylaniline slope is that observed in citric acid buffer (pH 5).

The results observed in the Tris Malonate buffer system at pH 7 for Chicago acid were much superior to those of the dimethylaniline and the hydroxynapthalenesulfonates. Chicago acid is more reactive both in the presence and absence of ascorbate. The activity at about pH 7.0 in terms of color development (ΔOD) per minute was about 3-4 times that in citric acid at pH 5.0 without ascorbate, and an even greater difference is seen with ascorbate. The results obtained in the presence of 56.8 μmol/l (1.0 mg/dl) of ascorbic acid at various times and their respective absorbance (optical density) values are graphically illustrated in FIG. 1 for MBTH/Chicago acid in Tris Malonate (pH 7) and citric acid (pH 5) systems. A comparison of results obtained with the various couplers in the presence of 56.8 μmol/l (1.0 mg/dl) of ascorbic acid is graphically illustrated in FIG. 2 for the Tris Malonate (pH 7) system, with one notable exception. Since the prior art coupler, dimethylaniline, would not even react under these parameters, its curve is taken from the citric acid (pH 5) data.

Thus, Chicago acid is optionally, and indeed optimally, functional in a preferred physiological pH range especially important in enzyme assays.

Although the invention has been described with a certain degree of particularity, it is understood that the present disclosure has been made only by way of example and that numerous changes in the details may be resorted to without departing from the scope of the invention.

What is claimed is:

1. Test means for the determination of an oxidizing substance which comprises an indicator system consisting essentially of a hydrazone and 8-amino-1-napthol-5,7-disulfonic acid.

2. The test means of claim 1 wherein said hydrazone is 3-methyl-2-benzothiazolinone hydrazone.

3. A test device for the determination of an oxidizing substance which comprises a carrier matrix and, incorporated therewith, the test means of claim 1.

4. A test device for the determination of an oxidizing substance which comprises a carrier matrix and, incorporated therewith, the test means of claim 2.

5. The test device of claim 3 wherein the carrier matrix is bibulous.

6. A test device for the determination of an oxidizing substance which comprises a tablet incorporated with the test means of claim 1.

7. A process for the preparation of a device for the determination of oxidizing substances which comprises incorporating a carrier matrix with the test means of claim 1.

8. The process of claim 7 wherein said incorporating is impregnating with a solution of said test means, followed by drying.

9. A process for determination of an oxidizing substance in a liquid sample which comprises contacting said sample with the test means of claim 1 and detecting any resultant response.

10. A process for determination of an oxidizing substance in a liquid sample which comprises contacting said sample with the test device of claim 3 and observing any resultant color change thereon.

11. In a test system for the determination of a constituent in a sample, having means responsive to the presence of said constituent in said sample to produce at least one oxidizing substance and having a composition for determining said at least one oxidizing substance, the improvement wherein said composition comprises an indicator system consisting essentially of a hydrazone and 8-amino-1-napthol-5,7-disulfonic acid.

12. The test system of claim 11 wherein said hydrazone is 3-methyl-2-benzothiazolinone hydrazone.

13. A test device which comprises a carrier matrix and, incorporated therewith, the test system of claim 11.

14. A test device which comprises a carrier matrix and, incorporated therewith, the test system of claim 12.

15. The device of claim 13 wherein the carrier matrix is bibulous.

16. A test device which comprises a tablet incorporated with the test system of claim 11.

17. A process for the preparation of a test device which comprises incorporating a carrier matrix with the test system of claim 11.

18. The process of claim 17 wherein said incorporating is impregnating with a solution of said test system, followed by drying.

19. A process for determination of a constituent in a liquid sample which comprises contacting said sample with the test system of claim 11 and observing any resultant color change.

20. A process for determination of a constituent in a liquid sample which comprises contacting said sample with the test device of claim 13 and observing any resultant color change.

* * * * *